US007816388B2

(12) United States Patent
Carminati et al.

(10) Patent No.: US 7,816,388 B2
(45) Date of Patent: Oct. 19, 2010

(54) BIOTIN DIAMINODERIVATIVES AND THEIR CONJUGATES WITH MACROCYCLIC CHELATING AGENTS

(75) Inventors: Paolo Carminati, Milan (IT); Mauro Ginanneschi, Prato (IT); Giovanni Paganelli, Forli-cesena (IT); Marco Chinol, Milan (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 10 days.

(21) Appl. No.: 12/065,833

(22) PCT Filed: Sep. 18, 2006

(86) PCT No.: PCT/EP2006/066440

§ 371 (c)(1),
(2), (4) Date: Jun. 12, 2008

(87) PCT Pub. No.: WO2007/039437

PCT Pub. Date: Apr. 12, 2007

(65) Prior Publication Data

US 2008/0249152 A1    Oct. 9, 2008

(30) Foreign Application Priority Data

Sep. 27, 2005    (EP)    ................... 05021034

(51) Int. Cl.
*A61K 31/4188*    (2006.01)
*C07D 235/00*    (2006.01)
(52) U.S. Cl. ..................................... 514/393; 548/302.7
(58) Field of Classification Search ............. 548/302.7; 514/393
See application file for complete search history.

(56) References Cited

U.S. PATENT DOCUMENTS

| 5,283,342 | A | 2/1994 | Gustavson |
| 5,608,060 | A | 3/1997 | Axworthy |
| 5,955,605 | A | 9/1999 | Axworthy |
| 2004/0241172 | A1 | 12/2004 | Axworthy et al. |

FOREIGN PATENT DOCUMENTS

| WO | 02066075 A | 8/2002 |
| WO | WO-02/066075 | * 8/2002 |

* cited by examiner

*Primary Examiner*—Rei-Tsang Shiao
*Assistant Examiner*—Janet L Coppins
(74) *Attorney, Agent, or Firm*—Lucas & Mercanti, LLP

(57) ABSTRACT

Formula (I) compounds are described: Formula (I) where the radicals are as defined in the description, processes for their preparation, and their uses for the preparation of conjugates with radionuclides for use in human and animal therapy and diagnostics, particularly for the diagnosis and therapy of pathological conditions such as tumors.

9 Claims, No Drawings

BIOTIN DIAMINODERIVATIVES AND THEIR CONJUGATES WITH MACROCYCLIC CHELATING AGENTS

FIELD OF THE INVENTION

The invention described herein relates to modified biotins useful for the preparation of conjugates with radionuclides for use in human and animal diagnostics and therapy, particularly for the diagnosis and treatment of pathological conditions such as tumours.

BACKGROUND OF THE INVENTION

Tumour therapy is mostly implemented through the use of substances targeted at destroying cancer cells. This can be achieved with cytotoxic substances, which have to penetrate into the tumour cells in order to exert their full effect, or by means of treatment of the tumour cells with radiation of sufficient energy to kill the cells. In both cases the main problem is to deliver the substance in a selective manner to the target cells, so as to avoid possible damage to the surrounding healthy cells. In the case of radiopharmaceuticals, i.e. substances carrying radioactive portions, the problem of selectively delivering the active part (that is, the radioactive portion) to the tumour target, avoiding as far as possible diffusion of the radionuclide in the body or interaction with healthy cells surrounding the tumour, is perceived as being particularly important.

For a discussion of all the issues involved and the solutions proposed to date, the reader is referred to U.S. Pat. Nos. 5,283,342, 5,608,060 and 5,955,605, assigned to NeoRx Corporation.

In these documents, the problem, amongst others, of the resistance of the molecule carrying the radionuclide to the metabolic attacks of the body is discussed. Specifically, the case most carefully studied is the molecule of biotin, which is one of the first choices for delivering the radionuclide to the tumour cells, thanks to its well-known interaction with avidins. Biotin is bound to the radionuclide-chelating portion, e.g. a molecule of tetra-azacyclododecanetetra-acetic acid [DOTA], via a linker. One of the main problems related to the use of biotin-DOTA conjugates is the resistance of the complex containing the biotin molecule, as connected to the radionuclide via the linker, to biotinidases, enzymes that break the peptide bond present in the complex. This peptide bond stems from the union of the chelating agent and biotin.

Among its much desired characteristics, this complex must be eliminated from the body rapidly and efficiently and must be sufficiently small (M.W.<1000) to allow easy distribution into the extracellular fluid where it will bind the tumour cells. In addition, it must show proven stability in vivo with only minimal uptake by non-tumour cells and rapid (renal) clearance and must not be metabolised.

Moreover, the chelating moiety must be such that it is not released in vivo, thus delivering potentially toxic compounds within the body. Experts in the field are clearly familiar with the problem of the release of radionuclide by the chelating portion, including metal ions which are entirely foreign to the body, which may be endowed with radioactivity of various types and even high-energy radiation, which is therefore highly damaging.

In a previous patent application from the same Applicant (WO 02/066075) our group reported the synthesis of a new biotin-DOTA conjugate together with binding, stability and affinity studies performed on this new derivative. The novelty of the new conjugate was that the amide carboxylic group was reduced to a methylene one thus generating the N-aminohexyl biotinamido derivative (r-BHD) in which the amide was transformed into a secondary amine without affecting the length of the biotin side-arm involved in Av/Sav binding. The DOTA ligand, in this compound, was directly linked to the amino group of the reduced biotin-hexamethylenediamine derivative through one of the four N-acetic side arms.

Moreover, the synthetic flexibility of r-BHD allows to generate a variety of new biotin derivatives for example with two DOTA chelators conjugated to the side-chain of biotin with the purpose to increase the efficacy of targeted radionuclide therapy by delivering higher radiation dose to the tumor.

US Patent application 2004/0241172, by Axworthy Donald B. et al., discloses biotin derivatives incorporating two DOTA groups, through specific linkers, which are directly bonded, through a benzyl group, to the core of DOTA molecules. This modification of the DOTA group could reduce the binding ability of the chelating moiety.

In order to improve the radiation/dose ratio we have designed and synthesized a new class of biotin derivatives.

DESCRIPTION OF THE INVENTION

The main object of the present invention is to provide new biotin derivatives that fulfill the requirement of an high ratio radiation/dose.

In particular the invention resides in a new class of biotin derivatives carrying two chelating groups per biotin molecule.

In this way using the same molar amount of biotin derivative, the radioactvity reaching the tumour cells is doubled.

One of the objects of the invention described herein is therefore a formula (I) compound as follows:

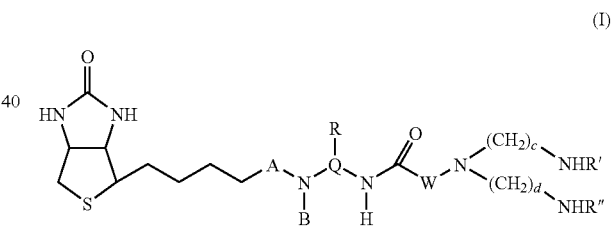

(I)

where:

A is $CH_2$ or CO;

B is H, CHO or COOH; with the proviso that:

when A is $CH_2$, Q is a —$(CH_2)_n$— group, in which n is an integer from 4 to 12, in which case R is absent; when A is CO, Q is selected from the group consisting of —$(CH_2)_a$—CH(R—)—$(CH_2)_b$—, where a and b are, independently, integers from 0 to n−1 and R is defined as below;

W is a $C_1$-$C_{12}$ alkylene or $C_2$-$C_{12}$ alkenylene linear chain or a functionalized polyethylene glycol; or a $C_6$-$C_{10}$ aromatic residue; or a glycofuranose residue; or W, alone or together with the nitrogen atom supporting the —$(CH_2)_c$—NHR' and —$(CH_2)_d$—NHR'' chains, is a heterocyclic group with 5 or 6 members containing one or more heteroatoms selected from O, N, S;

when W is an aromatic residue, an heterocyclic group or a sugar moiety, the nitrogen atom supporting the —$(CH_2)_c$—NHR' and —$(CH_2)_d$—NHR'' chains is optionally absent and the —$(CH_2)_c$—NHR' and —$(CH_2)_d$—NHR'' chains are directly and independently bonded to the carbon or nitrogen atoms of the aromatic and heterocyclic rings or to oxygen atoms of the glycofuranose residue;

c and d independently are integers from 3 to 10;

R' and R" are, independently, -Λ, where -Λ is a formula (II) macrocycle:

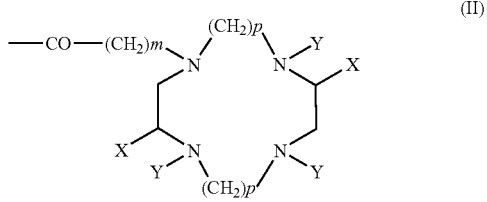

where Y are the same or different and are selected from the group consisting of hydrogen, linear or branched $C_1$-$C_4$ alkyl —$(CH_2)_m$—COOH, where m is an integer from 1 to 3;

X is hydrogen, or the —$CH_2$—U group, where U is selected from methyl, ethyl, p-aminophenyl, or X is the —$(CHJ)_o$-Z group, where o is an integer from 1 to 5, J is hydrogen, methyl or ethyl, Z is a heterocyclic group with 5 or 6 members containing one or more heteroatoms selected from O, N—$R_1$, $R_1$ being a hydrogen atom or a linear or branched $C_1$-$C_4$ alkyl group, and S; or Z is selected from —$NH_2$, —NH—C(=NH—)—$NH_2$, or —S—$R_2$ where $R_2$ is a linear or branched $C_1$-$C_4$ alkyl group;

p is the integer 2 or 3;

R is selected from the group consisting of linear or branched $C_1$-$C_4$ alkyl, cycloalkyl, heterocycle or —$(CH_2)_q$-T, where T is selected from the group consisting of S—$CH_3$, —OH, or —COOH, and q is 0, 1 or 2.

Linear or branched $C_1$-$C_4$ alkyl group means methyl, ethyl, propyl, isopropyl, n-butyl, sec-butyl, iso-butyl or ter-butyl.

Heterocycle with 5 or 6 members is an aromatic or non-aromatic heterocycle having in the ring at least a heteroatom selected from O, N—$R_1$, or S, such as, for example, 2-, 3- or 4-pyridyl, or 2-, 4-, or 5-imidazolyl.

reduce the binding ability of the chelating moietyA first group of preferred compounds according to the invention consists in the formula (I) compounds where A is $CH_2$, B is H, Q is —$(CH_2)_n$—, where n is an integer from 4 to 8, preferably 6, c and d are both 3 or 6, R' and R" are -Λ where Y is always —$CH_2$—COOH; X is hydrogen, and p is 2.

A further object of the invention described herein consists in formula (I) compounds with radioisotopes for diagnostic and/or therapeutic use. Examples of these isotopes are: Fe-52, Mn-52m, Co-55, Cu-64, Ga-67, Ga-68, Tc-99m, In-111, I-123, I-125, I-131, P-32, Sc-47, Cu-67, Y-90, Pd-109, Ag-111, Pm-149, Re-186, Re-188, At-211, Bi-212, Bi-213, Rh-105, Sm-153, Lu-177, and Au-198.

A first group of preferred complexes according to the invention are those where, in the formula (I) compounds, A is $CH_2$, B is H, Q is —$(CH_2)_n$—, where n is an integer from 4 to 8, preferably 6, c and d are together 3 or 6, R' and R" are -Λ where Y is always —$CH_2$—COOH; X is hydrogen, p is 2 and the radioisotope is Y-90.

Further objects of the invention described herein are processes for the preparation of formula (I) compounds and their complexes with radiopharmaceuticals.

Further objects of the invention described herein are pharmaceutical and/or diagnostic compositions containing formula (I) compounds and their complexes as indicated above.

Other objects of the invention described herein are the use of formula (I) compounds and their complexes with radioisotopes as medicaments or diagnostic tools, particularly for the preparation of medicaments which are useful in tumour therapy or diagnosis.

These and other objects relating to the invention described herein will be illustrated in detail in the part that follows here below, also by means of experimental examples.

The compounds according to the invention described herein may be prepared according to the following scheme, including the steps of:

a) formation of an amide bond between the carboxyl group of biotin and a primary amine group of $H_2N$-Q-$NH_2$ diamine, the other primary amine group being suitably protected, for example, with a Boc group, if necessary; or, alternatively, the coupling could be performed with the α-α-$NH_2$ group of an α,ω-diamino acid (i.e. Lys), being the ω-amino group suitably protected.

b) deprotection of the primary amine group;

c) reduction of the amide group to an amine, if A is $CH_2$ group;

d) coupling of the amine with the N-protected N,N-bis-substituted glycine amines of formula (III) which can be

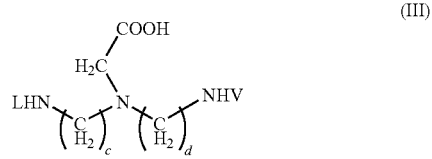

prepared by methods known to the operators skilled in the art;

where V and L are suitable protecting groups and c and range independently from 3 to 10;

e) conjugation with the desired formula (II) chelating agent -Λ.

Biotin is a commercial product, so as the amino acid Lys is. $H_2N$-Q-$NH_2$ diamines are available on the market and can in any event be prepared in several steps by using known methods.

The protection of the primary amine groups is easily achieved using suitable protective groups, such as, for example, Boc or Fmoc, and which in any event can be found from among those reported in the literature (see for instance: T. W. Greene, P. G. M. Wuts, "Protective groups in organic synthesis", 3rd Ed., J. Wiley & Sons, Inc., New York, 1999; Handbook of Reagents for Organic Synthesis, "Oxidizing and Reducing Agents", Edited by S. D. Burke and R. L. Danheiser, J. Wiley & Sons, Inc., New York, 1999).

Alternatively, the formula (I) compound, if A is CO group, can be prepared according to the above reported scheme devoid of the step c.

Activation of the —COOH group of biotin could be accomplished according to the known methods of peptide synthesis (P. Lloyd-Williams, F. Albericio, E. Giralt, "Chemical Approaches to the Synthesis of Peptides and Proteins", CRC Press, Boca Raton, New York, 1997); if the coupling is performed with an α,ω-diamino acid (i.e. Lys), the reaction can be carried out by anchoring the amino acid on a suitable resin, following the methods known in the solid phase peptide synthesis technique.

The conjugation of the compound according to the invention with the radioisotope to produce the complexes envisaged in the context of the invention described herein is carried out using the known traditional methods in the field, as described, for example, in Paganelli, Chinol et al. *European Journal of Nuclear Medicine* Vol. 26, No 4; April 1999; 348-357.

One of the preferred compounds of the invention is the one in which A is $CH_2$ group, Q is —$(CH_2)_n$—, where n is preferably 6, c=d are 3 or 6, R'=R" are -Λ where m is 1, Y is always —$CH_2$—COOH; X is hydrogen, p is 2 (DOTA chelating agent).

The process for preparing this preferred compound comprises the following steps:
a) formation of an amide bond between the carboxyl group of biotin and the primary amine group of hexamethylenediamine, suitably protected, for example with a Boc group, if necessary;
b) deprotection of the amine group of hexamethylenediamine;
c) reduction of the amide group to an amine group;
d) conjugation with the formula (III) amine where c=d=3 or 6, V=L are Fmoc protecting groups.
e) deprotection of the obtained amine;
f) conjugation with the chelator -Λ.

Step a) in the process according to the invention described herein consists in the formation of an amide bond between the biotin carboxyl group and the primary amine group of hexamethylenediamine-Boc. The biotin was treated with HATU to form an extremely active ester in situ that reacts with the amine group of hexamethylenediamine-Boc to form the relevant amide. This activation mechanism, which is used above all for peptide synthesis in the solid phase, requires a basic medium. To prevent the base from reacting with the active ester, tertiary organic bases such as di-isopropylethylamine (DIPEA) or N-methylmorpholin (NMM) are used. Protection of one of the two amine groups of hexamethylenediamine with Boc (ter-butyloxycarbonyl) is necessary to prevent the biotin binding to both ends of the diamine chain. The end product is isolated from the reaction medium after evaporation of the solvent (DMF) and precipitation with water. The product, recrystallised with propanol, was characterised by $^1$H-NMR, elemental analysis and ESI-MS. The reaction yield is around 88%.

In step b), biotinyl-hexamethylenediamine-Boc is solubilised in a mixture of AcOEt/HCl, approximately 3 M, to detach the Boc group. After removing the solvent mixture the product was lyophilised to completely eliminate HCl. The sample was purified by means of recrystallisation with an aqueous solution at basic pH and characterised by $^1$H-NMR and TLC.

In step c), the reduction of the amide group was done with $BH_3$THF. Since the reducing agent is extremely reactive, the process must be carried out in anhydrous conditions. The starting product was held under vacuum prior to the reaction and then solubilised in anhydrous THF (distilled with sodium and benzophenone). The reaction mixture was refluxed in a nitrogen atmosphere until complete reduction of the amide group (as monitored by $^1$H-NMR spectra) had taken place. After evaporating the solvent under reduced pressure, the reaction mixture was treated with an aqueous solution of HCl. After lyophilising the acid solution, the product was purified by recrystallisation from an aqueous solution at basic pH and then by reverse-phase column chromatography. Analysis of the product was done by analytical TLC which revealed its purity. The reaction yield is approximately 55%.

Step d) provided the conjugation reaction of the reduced biotinyl-hexamethylenediamine with the protected amine (III) by activation with the HATU/NMM system in NMP as solvent.

In step e) the Fmoc groups were removed by using the base piperidine.

Step f) provided the coupling of two DOTA groups, performed with the specific reagents for the formation of amide bonds in an aqueous medium: 1-(3-dimethylaminopropyl)-3-ethylcarbodiimide hydrochloride (EDC), and sulpho-NHS. DOTA (4 mole equiv respect to the biotin derivative) was dissolved in water and adjusted to a pH value suitable for activating mostly one of four carboxylic groups (G. Sabatino, M. Chinol, G. Paganelli, S. Papi, M. Chelli, G. Leone, A. M. Papini, A. DeLuca and M. Ginanneschi, *J. Med. Chem.* 2003, 46, 3170-3173). In this way, we can reduce the likelihood of obtaining side products. To the basic solution were added sulpho-NHS and lastly EDC. After the formation of the active ester in situ, the N,N-bis-alkylamino glycine derivative of the reduced biotinyl-hexamethylenediamine was added, checking that the pH of the solution remained around 7.5. Prepurification of the crude product was done by SPE (Solid Phase Extraction) and the purification was performed by means of semi-preparative RP-HPLC.

The objects of the invention described herein are pharmaceutical or diagnostic compositions containing as their active ingredient at least one formula (I) compound, also in the form of a complex with a radioisotope or, in the case of said formula (I) compound, in association with other active ingredients useful in the treatment of the diseases indicated in the invention described herein, e.g. other products possessing anticancer activity; also in separate dosage forms or in forms suitable for combined therapy. The active ingredient according to the invention will be in the form of a mixture along with suitable vehicles and/or excipients commonly used in pharmaceutical technology, such as, for example, those described in "Remington's Pharmaceutical Sciences Handbook", latest edition. The compositions according to the invention shall contain a therapeutically effective amount of the active ingredient. The dosages will be determined by the expert in the field, e.g. the clinician or primary care physician, according to the type of disease to be treated and the patient's condition, or concomitantly with the administration of other active ingredients.

Examples of pharmaceutical compositions are those that allow parenteral or loco-regional administration. Pharmaceutical compositions suitable for the purpose are solutions, suspensions, or lyophilised forms to be reconstituted at the time of use.

Forms suitable for the industrial application of the invention are kits for cancer radiotherapy, as, for example, described in European Patent 0 496 074, in the paper by Paganelli, Chinol et al. published in the *European Journal of Nuclear Medicine* Vol. 26, No 4; April 1999; 348-357, in U.S. Pat. No. 5,968,405 and in the relevant literature.

A further object of the invention described herein is a kit for the therapy or diagnosis of tumours by means of radioactivity. characterised in that at least one of the components of said kit contains a formula (I) compound or one of its complexes with a suitable radioisotope.

The compounds according to the invention are useful for the preparation of therapeutic and/or diagnostic agents for the treatment and diagnosis of tumours.

The compounds according to the invention, following the binding with radioisotopes for diagnostic and/or therapeutic use (as explained before), are useful to radiolabel preparations of avidin colloids for different medical applications.

For example, they can be used in tumour treatment methods with anticancer radiopharmaceuticals, such as, for example, those described in European Patent 0 496 074, in the paper by Paganelli, Chinol et al. published in the *European*

Journal of Nuclear Medicine Vol. 26, No 4; April 1999; 348-357, in U.S. Pat. No. 5,968,405 and in the relevant literature.

The following example further illustrates the invention.

EXAMPLE

Preparation of the BisDOTA-$C_3$—Compound 4

The preparation of Compound 4 was carried out following the steps herewith reported.

Synthesis of the Reduced Biotinamidohexylamine (r-BHD)—Compound 1

The detailed synthetic procedure and physico-chemical properties of Compound 1 were reported in the article by G. Sabatino, M. Chinol, G. Paganelli, S. Papi, M. Chelli, G. Leone, A. M. Papini, A. De Luca, and M. Ginanneschi, *J. Med. Chem.*, 2003, 46, 3170-3173. The NMR spectra of the products herewith reported were recorded in DMSO-$d_6$ solution on Varian 400. The N,N-bis[3-(Fmoc-amino)propyl]glycine of the example was purchased from Fluka (Switzerland) as potassium sulphate salt.

Synthesis of the r-BHD Conjugate with the N,N-bis[(3-amino)propyl]glycine—Compound 2

HATU (66.5 mg, 0.175 mmol, 0.7 mole eq.) in NMP (0.5 mL) were added to a solution of N,N-bis[3-(Fmoc-amino)propyl]glycine potassium sulphate (115.5 mg, 0.15 mmol, 0.6 mole eq.) and NMM (33.05 µL, 0.3 mmol, 1.2 mole eq.) in NMP (1 mL). This solution was dropwise added in 5 min to a suspension of r-BHD (Compound 1) (100 mg, 0.25 mmol) in NMP (5 mL) containing NMM (27.5 µL, 0.25 mmol, 1 mole eq.). The reaction mixture was stirred at room temp. monitoring the reaction by RP-HPLC (eluent: from 30% to 100% of B in 20 mim; $t_R$=13.4 min). After 2.5 h, Compound 1 (57.7 mg, 0.08 mmol, 0.3 mole eq.) was added again to the reaction mixture. After 2.5 h the reaction was stopped and the solvent evaporated under reduced pressure. The yellow-orange oil was suspended in water at 0° C. under stirring obtaining a white precipitate that was purified by RP-CC (LiChroprep RP-8, 40-63 µm; 170×20 mm; eluent: $CH_3CN/H_2O$/HCl=50:50:0.1, 1 mL/min) giving Compound 2 (130 mg; 55% yield). The Fmoc-protected bis-amino derivative (Compound 2) appeared to be pure by T.L.C. inspection ($CH_3CN$/$H_2O$/HCl=50:50:0.1). $^1$HNMR (200 MHz, DMSO): δ 9.63 (br s, 1H), 8.64 (br s, 3H), 7.87 (d, 4H), 7.65 (d, 4H), 7.43-7.27 (m, 8H), 6.41 (d, 2H), 4.31-4.14 (m, 8H), 3.85 (s, 2H), 3.14-3.03 (m, 11H), 2.82-2.76 (m, 4H), 2.6 (d, 2H), 1.76-1.25 (m, 20H) ESI-MS (m/e): calculated [M+H]$^+$ 944.5, found 944.5.

The Fmoc-protected bis-amine derivative (Compound 2) (88 mg, 0.09 mmol) was dissolved in DMF containing 25% of piperidine (5 mL). The solution was kept under stirring at room temp. for 6 h monitoring the reaction via RP-HPLC (from 30 to 100% B in 20 min; $t_R$=16.7 min). The reaction mixture was then evaporated under reduced pressure and the crude oil dissolved in the minimum amount of MeOH and precipitated with $Et_2O$. The collected solid was twice washed with ether, dissolved in water and lyophilised, affording a white product which was purified by SPE (Solid Phase Extraction; LiChroprep RP-18, 25-40 µm; 170×20 mm; eluent: $H_2O$ 100%-MeOH from 4 to 100%). The eluted fractions were collected and lyophilised giving de-protected bis-amine (Compound 3) (30 mg, 75% yield). $^1$HNMR (200 MHz, $CDCl_3$): δ 8.12 (br s, 2H), 6.45 (s, 2H), 4.26 (m, 1H), 4.12 (m, 1H), 3.59-2.95 (m, 7H), 2.95-2.70 (m, 12H), 2.50 (d, 2H), 1.80-1.20 (m, 20H) ESI-MS (m/e): calculated [M+H]$^+$ 443.6, found 443.1.

Conjugation of Compound 3 with the Activated DOTA for Obtaining BisDOTA-$C_3$ Compound 4

Sulpho-NHS (26 mg, 0.12 mmol) was added to a solution of DOTA-0.31$H_2O$ (49.2 mg, 0.12 mmol) in $H_2O$ (0.750 mL). The pH was then adjusted to 6.5 with 0.1 M NaOH and a solution of EDC (23 mg, 0.12 mmol) in $H_2O$ (0.5 mL) was added dropwise at 0° C.

The reaction mixture was stirred at 0° C. for 30 min and then a solution of Compound 3 (15 mg, 0.03 mmol) in $H_2O$ (0.750 mL), at pH 7.8, was added dropwise during 5 min.

The reaction was checked via RP-HPLC (from 5 to 100% of B in 30 min; $t_R$=16.4 min).

After 2 h the reaction mixture was lyophilized and the crude compound was pre-purified by SPE (Solid Phase Extraction; LiChroprep RP-18, 25-40 µm; 15×65 mm; eluents: a) $H_2O$; b) 4% MeOH in $H_2O$; c) 100% MeOH. HPLC test of the extracted fractions demonstrated that the Compound 4 was mainly in the fraction c. The methanolic solution was evaporated and the product purified by RP-HPLC (from 5 to 30% of B in 30 min: $t_R$=16.4 min) obtaining the pure Bis-DOTA (Compound 4) (15 mg, 24% yield) as a white solid.

ESI-MS: m/e calculated [M+H]$^+$ 1272.7, found 1272.7; [M−H]$^+$1270.7, found 1270.9. Anal. ($C_{56}H_{101}N_{15}O_{16}S$.6TFA.5$H_2O$) C, H, N.

Labelling tests, radiochemical purity, and serum stability tests were carried out with the compound illustrated in the foregoing example.

Labelling tests were carried out using 2 mg/mL MilliQ water solutions of BisDOTA-$C_3$. 1.0 mM sodium acetate buffer (pH 5.0) was added to BisDOTA-$C_3$, that were subsequently added with the radioisotope chloride solution ($MCl_3$, M=$^{111}$In, $^{90}$Y, $^{177}$Lu) at a specific activity of 1 mCi/7.2 µg. Finally these solutions were incubated at 95° C. for 30 min.

In order to determine Radiochemical Purity (RCP), Silica Gel Instant Thin Chromatography (ITLC-SG) was used. An aliquot of the radiolabelled mixture was added to a molar excess of Avidin and DTPA, then a drop was spotted on ITLC strips and developed with saline. The strip was analysed by a Radio-TLC apparatus; in this system, the complex formed by BisDOTA-$C_3$ and Avidin remains at the origin, while the unbound radiometal is complexed by DTPA and migrates with solvent front. RCP values typically obtained were >96%.

Stability assays were performed with and without ascorbic acid (AA) as radical scavenger. Aliquots from the labelled molecules were incubated at 37° C. with a 4-fold volume of saline or AA solution (4 mg/mL in 1.0 M sodium acetate buffer, pH 5.0). Stability studies were carried out at 24 and 48 hours and RCPs were calculated using ITLC-SG method as described before. Results showed that, in the presence of AA, the radiolabelled M-BisDOTA-$C_3$ were stable to radiolysis up to 48 hours.

The invention claimed is:
1. A compound of formula (I):

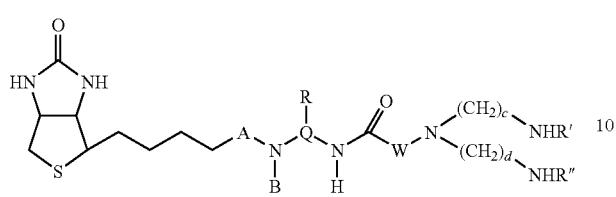

where:
A is $CH_2$ or CO;
B is H, CHO or COOH; with the proviso that:
when A is $CH_2$, Q is a —$(CH_2)_n$— group, in which n is an integer from 4 to 12, in which case R is absent; when A is CO, Q is selected from the group consisting of —$(CH_2)_a$—CH(R—)—$(CH_2)_b$—, where a and b are, independently, integers from 0 to n−1 and R is defined as below;
W is a $C_1$-$C_{12}$ alkylene or $C_2$-$C_{12}$ alkenylene linear chain or a functionalized polyethylene glycol; or a $C_6$-$C_{10}$ aromatic residue; or a glycofuranose residue; or
W, alone or together with the nitrogen atom supporting the —$(CH_2)_c$—NHR' and —$(CH_2)_d$—NHR" chains, is a heterocyclic group with 5 or 6 members containing one or more heteroatoms selected from O, N, S;
when W is an aromatic residue, an heterocyclic group or a sugar moiety, the nitrogen atom supporting the —$(CH_2)_c$—NHR' and —$(CH_2)_d$—NHR" chains is optionally absent and the —$(CH_2)_c$—NHR' and —$(CH_2)_d$—NHR" chains are directly and independently bonded to the carbon or nitrogen atoms of the aromatic and heterocyclic rings or to oxygen atoms of the glycofuranose residue;
c and d independently are integers from 3 to 10;
R' and R" are, independently, –Λ, where –Λ is a formula (II) macrocycle:

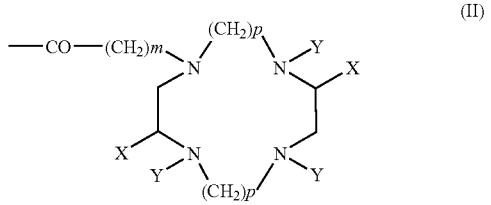

where Y are the same or different and are selected from the group consisting of hydrogen, straight or branched $C_1$-$C_4$ alkyl, —$(CH_2)_m$—COOH, where m is an integer from 1 to 3;
X is hydrogen, or the —$CH_2$—U group, where U is selected from methyl, ethyl, p-aminophenyl, or X is the —$(CHJ)_o$-Z group, where o is an integer from 1 to 5, J is hydrogen, methyl or ethyl, Z is a heterocyclic group with 5 or 6 members containing one or more heteroatoms selected from O, N—$R_1$, $R_1$ being a hydrogen atom or a linear or branched $C_1$-$C_4$ alkyl group, and S; or Z is selected from —$NH_2$, —NH—C(=NH—)—$NH_2$, or —S—$R_2$ where $R_2$ is a linear or branched $C_1$-$C_4$ alkyl group;
p is the integer 2 or 3;
R is selected from the group consisting of linear or branched $C_1$-$C_4$ alkyl, cycloalkyl, heterocycle or —$(CH_2)_q$-T, where T is selected from the group consisting of S—$CH_3$, —OH, or —COOH, and q is 0, 1 or 2.

2. The compound of Formula (I) according to claim 1, where independently A is $CH_2$, B is H, Q is —$(CH_2)_n$—, where n is an integer from 4 to 8, preferably 6, c and d are both 3 or 6, R' and R" are –Λ where Y is always —$CH_2$—COOH; X is hydrogen, and p is 2.

3. A complex of a compound of Formula (I) according to claim 1 with a radioisotope.

4. The complex according to claim 3, where the radioisotope is selected from the group consisting of Fe-52, Mn-52m, Co-55, Cu-64, Ga-67, Ga-68, Tc-99m, In-111, I-123, I-125, I-131, P-32, Sc-47, Cu-67, Y-90, Pd-109, Ag-111, I-131, Pm-149, Re-186, Re-188, At-211, Bi-212, Bi-213, Rh-105, Sm-153, Lu-177, and Au-198.

5. The complex according to claim 3, where Q is —$(CH_2)_n$—, n is an integer from 4 to 8, preferably 6, Y is —$CH_2$—COOH and the radioisotope is Y-90.

6. A pharmaceutical and/or diagnostic composition containing a compound according to claim 1 in a mixture with suitable vehicles and/or excipients.

7. A pharmaceutical and/or diagnostic composition containing a complex according to claim 3 in a mixture with suitable vehicles and/or excipients.

8. Kit comprising one pharmaceutical or diagnostic composition according to claim 6.

9. Kit comprising one pharmaceutical or diagnostic composition complex according to claim 3.

* * * * *